United States Patent [19]

Häbich et al.

[11] Patent Number: 5,147,865
[45] Date of Patent: Sep. 15, 1992

[54] PHOSPHONOPYRROLIDINE- AND PIPERIDINE-CONTAINING PSEUDOPEPTIDES OF THE STATIN TYPE, A PROCESS FOR THEIR PREPARATION AND THEIR USE AS MEDICAMENTS AGAINST RETROVIRUSES

[75] Inventors: Dieter Häbich; Jutta Hansen, both of Wuppertal; Arnold Paessens, Haan, all of Fed. Rep. of Germany

[73] Assignee: Bayer Aktiengesellschaft, Leverkusen, Fed. Rep. of Germany

[21] Appl. No.: 746,272

[22] Filed: Aug. 15, 1991

[30] Foreign Application Priority Data

Aug. 23, 1990 [DE] Fed. Rep. of Germany ....... 4026614

[51] Int. Cl.⁵ .................. A61K 37/16; A61K 31/675

[52] U.S. Cl. ........................................ 514/91; 514/7; 514/79; 514/82; 514/85; 514/89; 514/90; 514/92; 514/93; 514/94; 544/129; 544/337; 546/22; 548/412

[58] Field of Search ............. 544/58, 337; 546/22; 548/412; 514/7, 79, 82, 85, 89, 90-94

[56] References Cited

FOREIGN PATENT DOCUMENTS 346847 12/1989 European Pat. Off. .
352000 1/1990 European Pat. Off. .
356223 2/1990 European Pat. Off. .
357332 3/1990 European Pat. Off. .

*Primary Examiner*—Cecilia Tsang
*Attorney, Agent, or Firm*—Sprung Horn Kramer & Woods

[57] ABSTRACT

The invention relates to new phosphonopyrrolidine- and piperidine-containing pseudopeptides, to a process for their preparation and to their use as medicaments, in particular as antiviral agents in human and veterinary medicine.

4 Claims, No Drawings

PHOSPHONOPYRROLIDINE- AND PIPERIDINE-CONTAINING PSEUDOPEPTIDES OF THE STATIN TYPE, A PROCESS FOR THEIR PREPARATION AND THEIR USE AS MEDICAMENTS AGAINST RETROVIRUSES

The invention relates to new phosphonopyrrolidine- and piperidine-containing pseudopeptides, to a process for their preparation and to their use as medicaments, in particular as antiviral agents in human and veterinary medicine.

It has already been attempted to employ pseudopeptides, which in some cases also have renin-inhibitory activity, in combating AIDS [cf. GB A2 203,740; EP 337,714; EP 342,541; EP 346,847 and EP 352,000; EP 354,522; EP 357,332; EP 356,223].

The present invention relates to new phosphonopyrrolidine- and piperidine-containing pseudopeptides of the general formula (I)

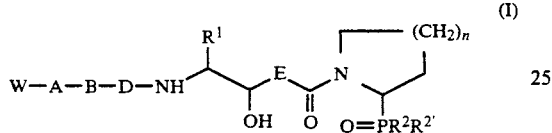

in which
W
represents hydrogen or a typical amino protecting group, or
represents straight-chain or branched alkyl or alkenyl in each case having up to 6 carbon atoms, which are optionally substituted by aryl having 6 to 10 carbon atoms, or
represents a group of the formula $R^3$—CO—, $R^5R^4N$—CO— or $R^6$—$SO_2$—,
in which
$R^3$
denotes hydrogen, trifluoromethyl or straight-chain or branched alkoxy having up to 8 carbon atoms or alkyl having up to 18 carbon atoms, each of which is optionally monosubstituted or disubstituted by aryl having 6 to 10 carbon atoms or pyridyl, or
denotes aryl having 6 to 10 carbon atoms, which is optionally substituted by halogen, trifluoromethyl, trifluoromethoxy or by straight-chain or branched alkyl having up to 8 carbon atoms,
denotes cycloalkyl having 3 to 7 carbon atoms, or
denotes quinolyl, indolyl, pyridyl, morpholino or piperazinyl, or
denotes a radical of the formula

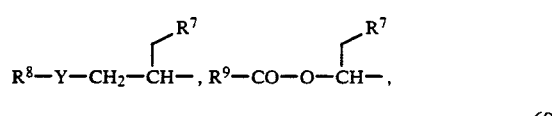

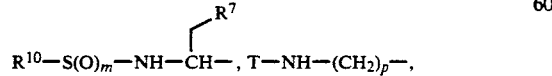

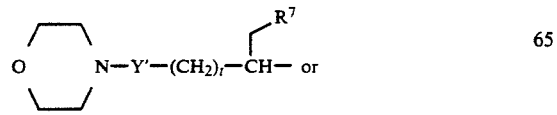

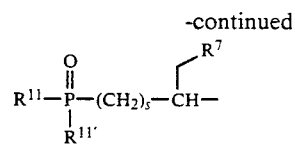

in which
$R^7$ denotes phenyl or naphthyl,
$R^8$, $R^9$ and $R^{10}$ are identical or different and denote straight-chain or branched alkyl having up to 17 carbon atoms, which is optionally substituted by phenyl or naphthyl, or denote aryl having 6 to 10 carbon atoms, which is in turn substituted by alkyl having up to 4 carbon atoms,
m denotes a number 0, 1 or 2,
T denotes morpholino or cyclohexyl,
p denotes a number 1, 2 or 3,
Y and Y' are identical or different and denote the CO or $SO_2$ group,
t denotes a number 0 or 1,
$R^{11}$ and $R^{11'}$ are identical or different and denote hydroxyl or alkoxy having up to 8 carbon atoms,
s denotes a number 1 or 2,
$R^4$ and $R^5$ are identical or different and
denote hydrogen or
denote aryl having 6 to 10 carbon atoms, which is optionally substituted by straight-chain or branched alkyl having up to 6 carbon atoms or halogen, or
denote cycloalkyl having 3 to 7 carbon atoms, or
denote straight-chain or branched alkyl having up to 18 carbon atoms,
$R^6$ denotes straight-chain or branched alkyl having up to 4 carbon atoms or phenyl which can in turn be substituted by methyl,
A, B and D are identical or different and
represent a direct bond or
represent a radical of the formula

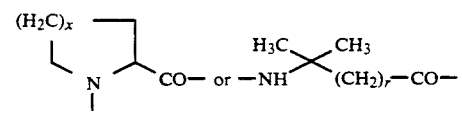

in which
x denotes the number 1 or 2 and
r denotes the number 0 or 1, or
represent a group of the formula

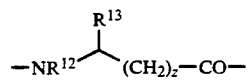

in which
z denotes the number 0 or 1,
$R^{12}$ denotes hydrogen or straight-chain or branched alkyl having up to 4 carbon atoms,
$R^{13}$ denotes hydrogen, cycloalkyl having 3 to 8 carbon atoms or aryl having 6 to 10 carbon atoms, or
denotes straight-chain or branched alkyl having up to 8 carbon atoms, which is optionally substituted by methylthio, hydroxyl, mercapto, guinidyl or by a group of the formula —$NR^{14}R^{15}$ or $R^{16}$—OC—, $R^{14}$ and $R^{15}$ are identical or different and denote hydrogen, straight-chain or branched alkyl having up to 8 carbon atoms or phenyl, and $R^{16}$ denotes hydroxyl, benzyloxy, alkoxy having up to 6 carbon atoms or the abovementioned group —$NR^{14}R^{15}$, or which is optionally substituted by cycloalkyl having 3 to 8 carbon atoms or by aryl having 6 to 10 carbon atoms, which in turn is substituted by hydroxyl, halogen, nitro, alkoxy having up to 8 carbon atoms or by the group —$NR^{14}R^{15}$, in which $R^{14}$ and $R^{15}$ have the abovementioned meaning, or which is optionally substituted by a 5- or 6-membered nitrogen-containing heterocycle or indolyl, in which the corresponding —NH functions are optionally protected by alkyl having up to 6 carbon atoms or by an amino protecting group, $R^1$, represents straight-chain or branched alkyl or alkenyl having up to 10 carbon atoms, which are optionally substituted by cycloalkyl having 3 to 8 carbon atoms or by aryl having 6 to 10 carbon atoms, which can in turn be substituted by halogen, nitro, hydroxyl, amino or straight-chain or branched alkoxy having up to 4 carbon atoms, n represents the number 1 or 2, $R^2$ and $R^{2'}$ are identical or different and represent hydroxyl or alkoxy having up to 8 carbon atoms, and E represents a radical of the formula >$CH_2$, $CF_2$ or >CH—$OR_{17}$, in which $R^{17}$ denotes hydrogen or straight-chain or branched alkyl having up to 4 carbon atoms, and their physiologically acceptable salts.

The compounds of the general formula (I) according to the invention have several asymmetric carbon atoms. They can be present independently of one another in the D- or the L- form. The invention includes the optical antipodes as well as the isomer mixtures or racemates. Preferably, the groups A, B and D are present independently of one another in the optically pure form, preferably in the L-form.

The radical of the general formula (VIII)

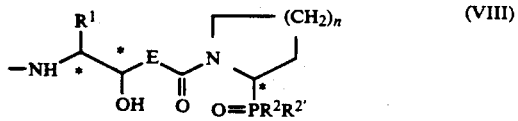

(VIII)

has, depending on the meaning of the radical E, 3 or 4 asymmetric carbon atoms (*), which can be present independently of one another in the R- or S-configuration.

Amino protecting groups in the context of the invention are the amino protecting groups customary in peptide chemistry. These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitrophrnoxycarbonyl, fluorenyl-9-methoxycarbonyl, formyl, acetyl, propionyl, pivaloyl, 2-chloroacetyl, 2- bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene.

The compounds of the general formula (I) according to the invention can be present in the form of their salts. These can be salts with inorganic or organic acids or bases.

Preferred compounds of the general formula (I) are those in which

W
represents hydrogen, tert-butyloxycarbonyl (BOC), 9-fluorenylmethyloxycarbonyl (Fmoc) or benzyloxycarbonyl or represents straight-chain or branched alkyl or alkenyl in each case having up to 4 carbon atoms, which are optionally substituted by phenyl, or represents a group of the formula $R^3$—CO—, $R^5R^4N$—CO— or $R^6$—$SO_2$—, in which $R^3$ denotes hydrogen, trifluoromethyl or straight-chain or branched alkoxy having up to 4 carbon atoms or alkyl having up to 16 carbon atoms, each of which is optionally monosubstituted or disubstituted by phenyl, naphthyl or pyridyl, or denotes phenyl or naphthyl, which are optionally substituted by fluorine, chlorine, trifluoromethyl, trifluoromethoxy or by straight-chain or branched alkyl having up to 6 carbon atoms, denotes cyclopropyl, cyclopentyl, cyclohexyl, quinolyl, indolyl, pyridyl, morpholino or piperazinyl, or denotes a radical of the formula

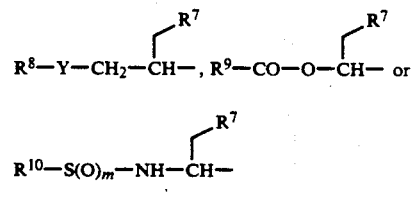

in which

Y denotes the CO or $SO_2$ group, $R^7$ denotes phenyl or naphthyl, $R^8$, $R^9$ and $R^{10}$ are identical or different and denote straight-chain or branched alkyl having up to 15 carbon atoms, tolyl, phenyl or naphthyl, m denotes a number 1 or 2, $R^4$ and $R^5$ are identical or different and denote hydrogen or denote phenyl or naphthyl, which are optionally substituted by straight-chain or branched alkyl having up to 4 carbon atoms, fluorine or chlorine, denote cyclopropyl, cyclopentyl or cyclohexyl, or denote straight-chain or branched alkyl having up to 16 carbon atoms, $R^6$ denotes phenyl which is substituted by methyl, A, B and D are identical or different and
represent a direct bond or
represent proline, or
represent a radical of the formula

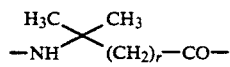

in which
r denotes the number 0 or 1,
represent a group of the formula

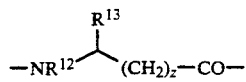

in which
z denotes the number 0 or 1,
$R^{12}$ denotes hydrogen, methyl or ethyl,
$R^{13}$ denotes hydrogen, cyclopentyl, cyclohexyl or phenyl,
or denotes straight-chain or branched alkyl having up to 6 carbon atoms, which can optionally be substituted by methylthio, hydroxyl, mercapto, guanidyl, amino, carboxyl or $H_2N—CO—$, or is substituted by cyclohexyl, naphthyl or phenyl, each of which can in turn be substituted by fluorine, hydroxyl, nitro or alkoxy having up to 4 carbon atoms,
or is substituted by indolyl, imidazolyl, pyridyl, triazolyl or pyrazolyl, where the corresponding —NH functions are optionally protected by alkyl having up to 4 carbon atoms or by an amino protecting group, $R^1$ represents straight-chain or branched alkyl or alkenyl having up to 8 carbon atoms, which are optionally substituted by cyclopropyl, cyclobutyl, cyclopentyl, cyclohexyl, cycloheptyl or phenyl, each of which is in turn substituted by fluorine, chlorine, bromine, nitro, hydroxyl or amino, n represents the number 1 or 2, $R^2$ and $R^{2'}$ are identical or different and represent hydroxyl or alkoxy having up to 6 carbon atoms, and E represents a radical of the formula $>CH_2$, $>CF_2$ or $>CH—OR^{17}$,
in which
$R^{17}$ denotes hydrogen or straight-chain or branched alkyl having up to 4 carbon atoms, and their physiologically acceptable salts.

Particularly preferred compounds of the general formula (I) are those in which

W
represents hydrogen, tert-butyloxycarbonyl (BOC) or benzyloxycarbonyl, or
represents allyl or benzyl,
represents a group of the formula $R^3—CO—$, $R^5R^4N—CO—$ or $R^6—SO_2—$,
in which
$R^3$ denotes hydrogen, trifluoromethyl or straight-chain or branched alkyl having up to 14 carbon atoms, each of which is optionally monosubstituted or disubstituted by phenyl, naphthyl or pyridyl, or denotes phenyl or naphthyl, which are optionally substituted by fluorine, chlorine, trifluoromethyl, trifluoromethoxy or by straightchain or branched alkyl having up to 4 carbon atoms, denotes cyclopropyl, cyclopentyl, cyclohexyl, quinolyl, indolyl, pyridyl, morpholino or piperazinyl, or
denotes a radical of the formula

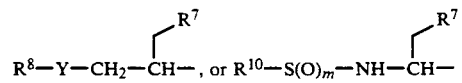

in which
Y denotes the CO or $SO_2$ group,
$R^7$ denotes phenyl or naphthyl,
$R^8$ and $R^{10}$ are identical or different and denote straight-chain or branched alkyl having up to 14 carbon atoms, tolyl, phenyl or naphthyl,
m denotes a number 1 or 2,
$R^4$ and $R^5$ are identical or different and
denote hydrogen or
denote phenyl or naphthyl, which are optionally substituted by methyl, fluorine or chlorine,
denote cyclopropyl, cyclopentyl or cyclohexyl, or
denote straight-chain or branched alkyl having up to 14 carbon atoms, $R^6$ denotes phenyl which is substituted by methyl, A, B and D are identical or different and
represent a direct bond, or
represent proline, or
represent a radical of the formula

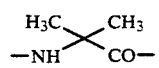

represent a group of the formula

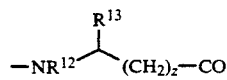

in which
Z denotes the number 0 or 1,
$R^{12}$ denotes hydrogen or methyl,
$R^{13}$ denotes hydrogen, cyclopentyl or cyclohexyl, or denotes straight-chain or branched alkyl having up to 4 carbon atoms, which is optionally substituted by methylthio, hydroxyl, mercapto, guanidyl, amino, carboxyl or $H_2N—CO—$, or is substituted by cyclohexyl, naphthyl or phenyl, each of which can in turn be substituted by hydroxyl, fluorine, chlorine or alkoxy having up to 4 carbon atoms, or is substituted by indolyl, imidazolyl, triazolyl, pyridyl or pyrazolyl, where the NH benzyloxymethylene or t-butyloxycarbonyl (Boc), $R^1$ represents straight-chain or branched alkyl having up to 6 carbon atoms, which is optionally substituted by cyclopropyl, cyclopentyl, cyclohexyl or phenyl, each of which can in turn be substituted by hydroxyl, n represents the number 1 or 2, $R^2$ and $R^{2'}$ are identical or different and represent hydroxyl or alkoxy having up to 4 carbon atoms, and E represents the >CH$_2$ or the >CHOH group and their physiologically acceptable salts.

A process for the preparation of the compounds according to the invention of the general formula (I)

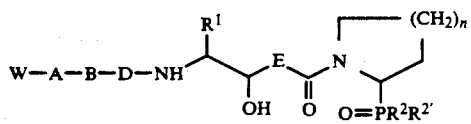
(I)

in which

W, A, B, D, $R^1$, $R^2$, $R^{2'}$, E and n have the abovementioned meaning, has additionally been found, characterised in that

[A] compounds of the general formula (Ia)

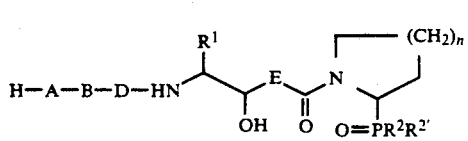
(Ia)

in which

A, B, D, $R^1$, $R^2$, $R^{2'}$, E and n have the abovementioned meaning, are reacted with compounds of the general formulae (II) or (III):

W—X (II)

(W')$_2$O (III)

in which

W has the abovementioned meaning

X represents halogen, preferably chlorine, and

W' represents the group CF$_3$CO or CH$_3$CO, by the conditions customary in peptide chemistry, in inert solvents, in the presence of a base, or

[B] either compounds of the general formula (Ib)

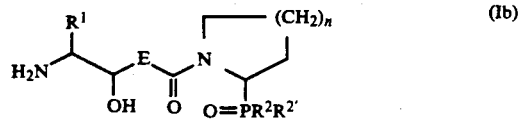
(Ib)

in which $R^1$, $R^2$, $R^{2'}$, E and n have the abovementioned meaning, are reacted directly with compounds of the general formula (IV)

W—A'—B'—D'—OH (IV)

in which

W has the abovementioned meaning,

A', B' or D' have the abovementioned meaning of A, B or D and do not simultaneously represent a bond, or compounds of the general formula (Ic)

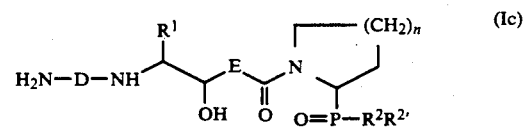
(Ic)

in which

D, $R^1$, $R^2$, $R^{2'}$, E and n have the abovementioned meaning, are reacted with compounds of the general formula (IVa) W—A'—B'—OH (IVa)

in which

W, A' and B' have the abovementioned meaning, with activation of the carboxylic acid, in inert solvents, if appropriate in the presence of a base and of an auxiliary, or

[C] compounds of the general formulae (V) and (VI)

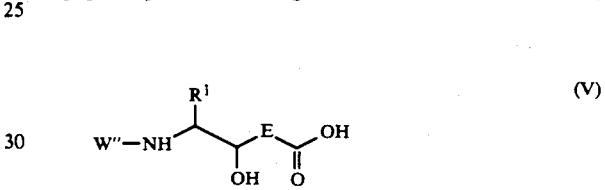
(V)

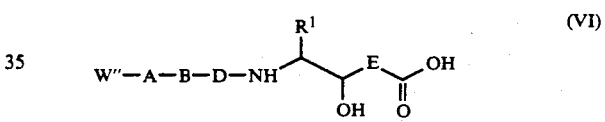
(VI)

in which $R^1$, W, A, B, D and E have the abovementioned meaning and

W''' represents an amino protecting group, preferably BOC, are condensed with compounds of the general formula (VII)

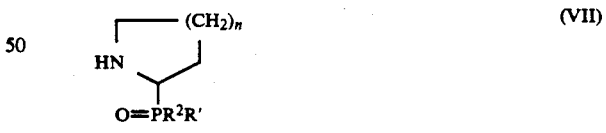
(VII)

in which $R^2$, $R^{2'}$ and n have the abovementioned meaning, with activation of the carboxylic acids, if appropriate in the presence of a base and of an auxiliary, and in the case of the compounds of the general formula (V), the protecting group W''' is then removed by a customary method and, if appropriate, reacted further with the compounds of the general formulae (IV) or (IVa) by the method described under process [B].

The process according to the invention can be illustrated by way of example by the following equation:

[A]
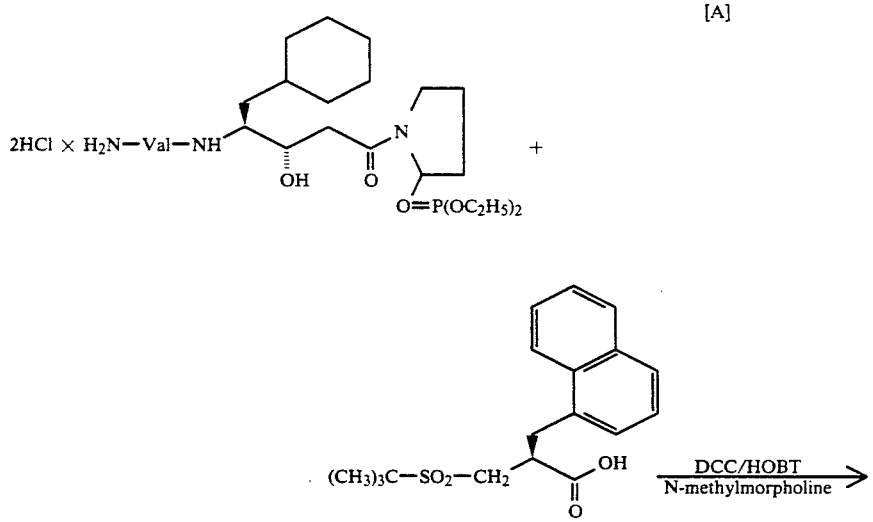
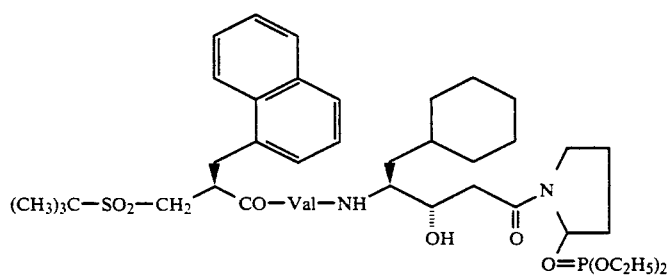
[B]
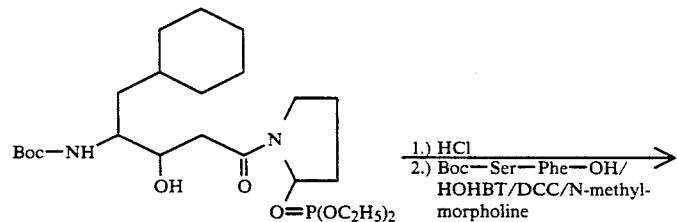
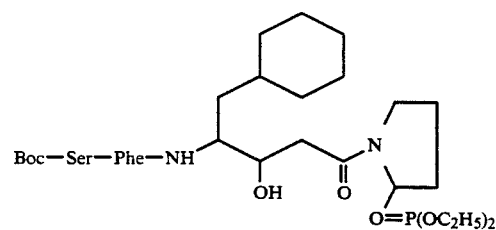
[C]
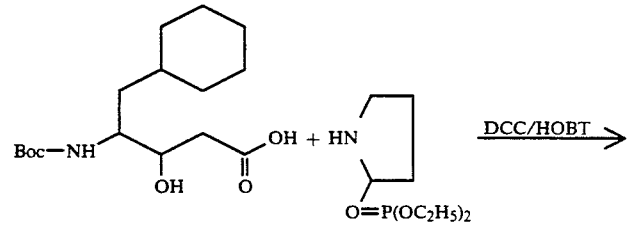

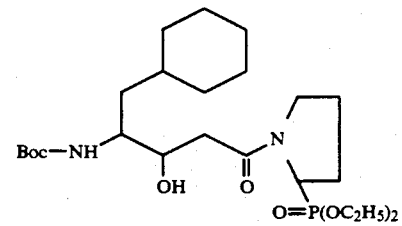

Suitable solvents for all process steps are the customary inert solvents which do not change under the reaction conditions. These preferably include organic solvents such as ethers, for example diethyl ether, glycol monomethyl ether or glycol dimethyl ether, dioxane or tetrahydrofuran, or hydrocarbons such as benzene, toluene, xylene, cyclohexane or mineral oil fractions or halogenohydrocarbons such as methylene chloride, chloroform, carbon tetrachloride, or dimethyl sulphoxide, dimethylformamide, hexamethylphosphoric triamide, ethyl acetate, pyridine, triethylamine or picolines. It is also possible to use mixtures of the solvents mentioned.

Dichloromethane, chloroform, dimethylformamide or tetrahydrofuran are particularly preferred.

The compounds of the general formulae (IV) and (IVa) are known per se and can be prepared by reaction of an appropriate fragment, composed of one or more amino acid groups, having a free carboxyl group which, if appropriate, is present in activated form, with a complementary fragment, composed of one or more amino acid groups, having an amino group, if appropriate in activated form, and by repeating this process with appropriate fragments, protecting groups can then be removed if appropriate or replaced by other protecting groups [cf. Houben-Weyl, Methoden der organischen Chemie, Synthese von Peptiden II (Methods of Organic Chemistry, Synthesis of Peptides Stuttgart].

Auxiliaries employed for the peptide couplings for the introduction of the substituent W (formulae (II) and (III)) and of the phosphonopyrrolidine and piperidine ring (formula (VII)) are preferably condensing agents which can also be bases, in particular if the carboxyl group is activated as the anhydride. The customary condensing agents are preferred here, such as carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphate.

Bases which can be employed both in the peptide couplings and in the abovementioned reactions with the compounds of the general formulae (II), (III) and (IV) are alkali metal carbonates, for example sodium carbonate or potassium carbonate or sodium hydrogencarbonate or potassium hydrogencarbonate, or organic bases such as trialkylamines, for example triethylamine, N-ethylmorpholine, N-methylpiperidine or N-methylmorpholine. N-Methylmorpholine is preferred.

The auxiliaries and bases are employed in an amount of 0.5 mol to 4 mol, preferably 1 to 1.5 mol, in each case relative to 1 mol of the compounds of the general formulae (II), (III), (IV), (IVa) and (VII).

The peptide couplings, the introduction of the substituent W (II, III) and the reaction with compounds of the general formula (VII) are carried out in a temperature range from 0° C. to 100° C., preferably at 0° C. to 30° C. and at normal pressure.

The reactions can be carried out both at normal pressure and at elevated or reduced pressure (for example 0.5 to 5 bar), preferably at normal pressure.

The compounds of the general formulae (Ia), (Ib) and (Ic) are also new and can be prepared by the methods mentioned above under the respective processes [A]or [B].

The compounds of the general formulae (II) and (III) are known or can be prepared by a customary method.

The compounds of the general formulae (V) and (VI) ar known in some cases or are new and in the latter case can prepared starting from the corresponding esters by hydrolysis according to a customary method [cf. J. Med. Chem. 28, 1779 (1985), J. O., 43, 3624 (1978), J. Med. Chem. 23, 27 (1980); J. Med. Chem. 29, 2080 (1986); EP 184 855; PCT WO 87 04349].

The compounds of the general formula (VII) are also known [n=1 cf. U.S. Pat. No. 4,186,268; Y. Nomura et al., Chem. Lett., 693 (1977); n=2 cf. V. A. Solodenko et al., Zh. Obshch. Khim. 57, 2392 (1987)].

It has surprisingly been found that the compounds of the general formula (I) have an extremely strong action against retroviruses. This is confirmed using an HIV-specific protease enzyme test.

The results for the examples listed below were determined by the HIV test system described in the following literature reports [cf. Hansen, J., Billich, S., Schulze, T., Sukrow, S. and Mölling, K. (1988), EMBO Journal, Vol. 7, No. 6, pages 1785-1791]: purified HIV protease was incubated with synthetic peptide which imitated a cleavage site in the Gag precursor protein and represented an in vivo cleavage site of the HIV protease. The resulting cleavage products of the synthetic peptide were analysed by means of reverse phase high performance liquid chromatography (RP-HPLC). The $IC_{50}$ values given relate to the substance concentration which causes a 50% inhibition of protease activity under the abovementioned test conditions.

| Example No. | $IC_{50}$ (RP-HPLC) (M) |
|---|---|
| 5 | $10^{-5}$ |
| 9 (polar) | $10^{-4}$ |
| 11 | $10^{-4}$ |
| 12 | $10^{-4}$ |
| 14 | $5 \times 10^{-7}$ |
| 15d | $10^{-5}$ |
| 15e | $5 \times 10^{-7}$ |
| 15f | $10^{-6}$ |
| 15m | $5 \times 10^{-6}$ |

| Example No. | IC$_{50}$ (RP-HPLC) (M) |
|---|---|
| 15n | $10^{-5}$ |
| 18 | $10^{-5}$ |
| 25 (polar) | $10^{-7}$ |
| 28 | $10^{-5}$ |

The compounds according to the invention additionally showed action in cell cultures infected with lentivirus.

It was possible to show this by the example of the HIV virus.

The HIV test was carried out with slight modifications by the method of Pauwels et al. (Journal of Virological Methods 20 (1988) 309–321).

Normal human blood lymphocytes (PBLs) were concentrated by means of Ficoll-Hypaque and stimulated with phytohaemagglutinin (90 µg/ml) and interleukin 2 (40 U/ml) in RPMI 1640 and 20% foetal calf serum. For infection with the infectious HIV, PBLs were pelleted and the cell pellet was then suspended in 1 ml of HIV virus adsorption solution and incubated at 37° C. for 1 hour.

The virus adsorption solution was centrifuged and the infected cell pellet was taken up in growth medium such that a concentration of $1 \times 10^5$ cells per ml was established. The cells infected in this way were pipetted into the wells of 96-well microtitre plates at a concentration of $1 \times 10^4$ cells/well.

The first vertical row of the microtitre plate contained only growth medium and cells which had not been infected, but otherwise treated exactly as described above (cell control). The second vertical row of the microtitre plate contained only HIV-infected cells (virus control) in growth medium. The other wells contained the compounds according to the invention at different concentrations, starting from the wells of the 3rd vertical row of the microtitre plate, from which the test compounds were diluted 10 times in two-fold steps.

The test batches were incubated at 37° C. until, in the untreated virus control, the syncytia formation typical for HIV occurred (between day 3 and 6 after infection), which was then evaluated microscopically. In the untreated virus control, about 20 syncytia resulted under these test conditions, while the untreated cell control exhibited no syncytia.

The IC-50 values were determined as the concentration of the treated and infected cells at which 50% (about 10 syncytia) of the virus-induced syncytia were suppressed by treatment with the compound according to the invention.

| Example No. | IC$_{50}$ (µM) |
|---|---|
| 9 | 1.5 |
| 16 | 4.3 |

It was found that the compounds according to the invention protect HIV-infected cells from virus-induced cell destruction.

The compounds according to the invention are suitable as active compounds in human and veterinary medicine for the treatment and prophylaxis of diseases caused by retroviruses.

Examples of indication areas which can be mentioned in human medicine are:

1. The treatment or prophylaxis of human retrovirus infections.
2. For the treatment or prophylaxis of diseases (AIDS) caused by HIV I (human immunodeficiency virus; earlier called HTLV III/LAV) and by HIV II and the stages associated therewith such as ARC (AIDS-related complex) and LAS (lymphadenopathy syndrome) and also the immunodeficiency and encephalopathy caused by this virus.
3. For the treatment or the prophylaxis of an HTLV I or HTLV II infection.
4. For the treatment or the prophylaxis of the AIDS-carrier state (AIDS-transmitter state).

Examples of indications in veterinary medicine which can be mentioned are:

Infections with a) Maedi-visna (in sheep and goats)
b) progressive pneumonia virus (PPV) (in sheep and goats)
c) caprine arthritis encephalitis virus (in sheep and goats)
d) Zwoegerziekte virus (in sheep)
e) infectious anaemia virus (of the horse)
f) infections caused by the feline leukaemia virus.
g) infections caused by the feline immunodeficiency virus.

The abovementioned items 2, 3 and 4 are preferred from the indication area in human medicine.

The present invention includes pharmaceutical preparations which contain one or more compounds of the formula (I) or which consist of one or more active compounds of the formula (I) in addition to non-toxic, inert pharmaceutically suitable excipients, and processes for the production of these preparations.

The active compounds of the formula (I) are intended to be present in the abovementioned pharmaceutical preparations, preferably in a concentration of about 0.1 to 99.5, preferably from about 0.5 to 95% by weight, of the total mixture.

The abovementioned pharmaceutical preparations may also contain other pharmaceutical active compounds in addition to the compounds of the formula (I).

The abovementioned pharmaceutical preparations are prepared in a customary manner by known methods, for example by mixing the active compound or compounds with the excipient or excipients.

In general, it has proved advantageous both in human and in veterinary medicine to administer the active compound or compounds of the formula (I) in total amounts from about 0.5 to about 500, preferably 5 to 100 mg/kg of body weight every 24 hours, if desired in the form of several individual doses, in order to achieve the desired results. An individual dose contains the active compound or compounds preferably in amounts from about 1 to about 80, in particular 1 to 30 mg/kg of body weight. However, it may be necessary to deviate from the dosages mentioned, in particular depending on the species and the body weight of the subject to be treated, the nature and severity of the disease, the type of preparation and the administration of the medicament and the period or interval within which administration takes place.

APPENDIX TO THE EXPERIMENTAL SECTION

I. List of the eluent mixtures used for chromatography:
I. Dichloromethane:methanol
II. Toluene:ethyl acetate III. Acetonitrile:water
IV. Dichloromethane:methanol:ammonia 9:1:0.1

II. Amino acids

In general, the configuration is indicated by placing an L or D before the amino acid abbreviation, in the case of the racemate a D,L, it being possible, for simplification, to suppress the indication of configuration in the case of L-amino acids and explicit indication then only taking place in the case of the D-form or of the D,L-mixture.

| | |
|---|---|
| Ala | L-alanine |
| Arg | L-arginine |
| Asn | L-asparagine |
| Asp | L-aspartic acid |
| Cys | L-cysteine |
| Gln | L-glutamine |
| Glu | L-glutamic acid |
| Gly | L-glycine |
| His | L-histidine |
| Ile | L-isoleucine |
| Leu | L-leucine |
| Lys | L-lysine |
| Met | L-methionine |
| Pro | L-proline |
| Phe | L-phenylalanine |
| Ser | L-serine |
| Thr | L-threonine |
| Trp | L-tryptophan |
| Tyr | L-tyrosine |
| Val | L-valine |

III. Abbreviations

| | |
|---|---|
| AIB | aminoisobutyryl |
| Z | benzyloxycarbonyl |
| BOC | tert-butoxycarbonyl |
| CMCT | 1-cyclohexyl-3-(2-morpholinoethyl)-carbodiimide metho-p-toluenesulphonate |
| DCC | dicyclohexylcarbodiimide |
| DMF | dimethylformamide |
| HOBT | 1-hydroxybenzotriazole |
| Mir | miristoyl |
| Ph | phenyl |
| THF | tetrahydrofuran |

STARTING COMPOUNDS

EXAMPLE I

Boc—Aib—Phe—Val—OCH$_3$

A stirred solution, cooled to 0° C., of 10.17 g (50.0 mmol) of 2-(1,1-dimethylethoxycarbonyl)amino-2-methyl-propionic acid and 7.09 g (52.5 mmol) of HOBT in 140 ml of anhydrous dichloromethane was treated with 10.83 g (52.5 mmol) of DCC. The cooling bath was removed and the mixture was stirred at room temperature for 30 min. It was then cooled to 0° C. again, a solution of 17.47 g (55.5 mmol) of HCl×H—Phe—Val—OCH$_3$ and 13.75 ml (125.0 mmol) of N-methylmorpholine in 140 ml of dichloromethane was added and the mixture was stirred in a thawing ice bath for 15 h. The precipitated urea was removed by filtration, and the filtrate was washed with 2×100 g of NaHCO$_3$ solution and 100 ml of water and dried over MgSO$_4$. After evaporation of the solvent in vacuo and chromatography of the crude product on 270 g of silica gel (toluene:ethyl acetate 3:2), 20.0 g (86% of theory) of the title compound were obtained as a colourless foam.

TLC: R$_f$=0.38 (toluene : ethyl acetate 1:1).

MS (DCI, NH$_3$): m/e=464 (M+H)$^+$.

SF (MW): C$_{24}$H$_{37}$N$_3$O$_6$ (463.58),.

EXAMPLE II

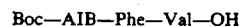

Boc—AIB—Phe—Val—OH

A solution of 13.0 g (28.0 mmol) of the compound from Example I in 10 ml of THF was treated with a solution of 2.35 g (56.0 mmol) of lithium hydroxide hydrate in 55 ml of water and the mixture was additionally stirred at 0° C. for 3 h. The reaction mixture was then poured into a mixture of 60 ml of water, 40 g of ice and 100 ml of ethyl acetate and adjusted to pH 3 by addition of 1N hydrochloric acid. The organic phase was separated off, aqueous phase was extracted with 50 ml of ethyl acetate and the combined organic extracts were dried over magnesium sulphate. After evaporation of the solvent in vacuo and treatment of the residue with 10 ml of ether and 30 ml of n-pentane, 10.3 g (82% of theory) of the title compound were obtained as colourless crystals.

Melting point: 157° C.

HPLC purity: >96%.

TLC: R$_f$=0.44 (acetonitrile:water=9:1).

MS (FAB): m/e=450 (M+H)$^+$, 472 (M+Na)$^+$.

SF (MW): C$_{23}$H$_{35}$N$_3$O$_6$ (449.55).

EXAMPLE III

Boc—AIB—Val—OCH$_3$

As described for Example I, 10.3 g (79% of theory) of the title compound were obtained as colourless crystals from 10.17 g (50.0 mmol) of 2-(1,1-dimethylethoxycarbonyl)amino-2-methylpropionic acid using 9.19 g (55.5 mmol) of HCl×H—Val—OCH$_3$ after chromatography of the crude product on 300 g of silica gel (toluene:ethyl acetate 1:1).

Melting point : 108° C.

TLC: R$_f$=0.43 (toluene:ethyl acetate=1:1).

MS (FAB): m/e=317 (M+H)$^+$.

SF (MW): C$_{15}$H$_{28}$N$_2$O$_5$ (316.40).

EXAMPLE IV

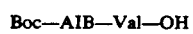

Boc—AIB—Val—OH

As described for Example II, 4.0 g (84% of theory) of the title compound were obtained as a colourless powder from 5.0 g (15.8 mmol) of the compound from Example III.

Melting point : 162° C.

TLC: R$_f$=0.5 (acetonitrile:water=9:1).

MS (FAB): m/e=309 (M+Li)$^+$, 617 (2M+2Li-H)$^+$.

SF (MW): C$_{14}$H$_{26}$N$_2$O$_5$ (302.38).

PREPARATION EXAMPLES

EXAMPLE 1

Diethyl 1-{(3R,4S)-4-[(tert-butoxycarbonyl)amino]-5-cyclohexyl-3-hydroxypentanoyl}-(2R,S)-2-(pyrrolidinyl)phosphonate

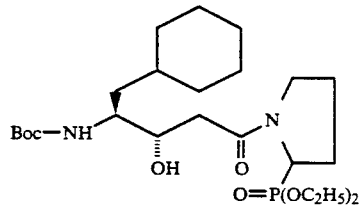

A stirred solution of 16.57 g. (52.53 mmol) of N-(tert-)butoxycarbonyl)-(3S, 4S)-4-amino-5-cyclohexyl-3-hydroxypentanoic acid [Boc-ACHPA; Boger et al., J. Med. Chem. 28, 1779 (1985)] in 100 ml of anhydrous DMF was treated at 0° C. with 7.80 g (57.78 mmol) of HOBT and 23.36 g (55.16 mmol) of CMTC. The cooling bath was removed and the mixture was subsequently stirred at room temperature for 1 h. It was then cooled to 0° C. again and a solution of 11.97 g (55.79 mmol) of diethyl 2(R,S)-2-(pyrrolidinyl)-phosphonate [U.S. Pat. No. 4,186,268] and 14.00 ml (127.14 mmol) of N-methylmorpholine was added dropwise in 30 ml of DMF. The cooling bath was removed and the mixture was subsequently stirred at room temperature for 17 h. The reaction mixture was then concentrated in vacuo and the residue was partitioned between 200 ml of water and 200 ml of ethyl acetate. The aqueous phase was extracted with 50 ml of ethyl acetate, and the combined extracts were washed with 100 ml of water and dried over MgSO$_4$. After evaporation of the solvent in vacuo and chromatography of the crude product on 800 g of silica gel (dichloromethane:methanol 95:5), 17.91 g (68% of theory) of the title compound were obtained as an oil.

R$_f$=0.12 eluent mixture I (95:5).
MS (FAB): m/e=505 (M+H)$^+$, 527 (M+Na)$^+$.

EXAMPLE 2

Diethyl 1-[(3R,4S)-4-amino-5-cyclohexyl-3-hydroxypentanoyl]-(2R,S)-2-(pyrrolidinyl)phosphonate hydrochloride

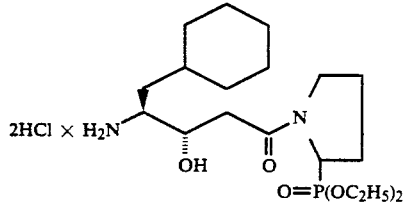

A solution of 17.95 g (35.57 mmol) of the compound from Example 1 in 178 ml of a 4N solution of gaseous hydrogen chloride in anhydrous dioxane was stirred at room temperature for 30 min. 20 ml of toluene were then added and the mixture was concentrated in vacuo. This process was repeated twice more, then the residue was triturated with a little ether, filtered off with suction and dried over KOH in a high vacuum. 14.75 g (87% of theory) of the title compound were obtained as a hygroscopic powder.

R$_f$=0.54, I (4:1).
MS (DCI, NH$_3$) m/e=405 (M+H)$^+$.

EXAMPLE 3

Diethyl 1-[(3R, 4S)-4-(tert-butoxycarbonylasparaginyl)amino-5-cyclohexyl-3-hydroxypentanoyl]-(2R,S)-2(pyrrolidinyl)phosphonate

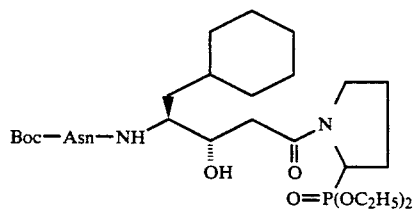

A stirred solution of 3.48 g (15.00 mmol) of tert-butoxycarbonylasparagine and 2.23 g (16.50 mmol) of HOBT in 30 ml of anhydrous DMF was treated at 0° C. with 6.67 g (15.75 mmol) of CMTC and the mixture was stirred for 2 h. A solution of 4.77 g (10.00 mmol) of the compound from Example 2 and 4.4 ml (40.00 mmol) of N-methylmorpholine in 15 ml of DMF were added dropwise to this at this temperature and the mixture was subsequently stirred in a thawing ice bath for 17 h. The reaction mixture was then concentrated in vacuo and the residue was partitioned between 50 ml of ethyl acetate and 50 ml of water. The aqueous phase was extracted with 30 ml of ethyl acetate and the combined extracts were washed with 50 ml of water and dried over MgSO$_4$. After evaporation of the solvent in vacuo and chromatography of the residue on 80 g of silica gel (dichloromethane methanol 9:1), 3.88 g (63% of theory) of the title compound were obtained as a foam.

R$_f$=0.30, I (95:5).
MS (FAB): m/e=619 (M+H)$^+$, 641 (M+Na)$^+$.

TABLE 1

| Example No. | A—B | Yield (%) | MS (FAB) m/e (M + H)$^+$ | R$_f$/eluent (ratio) |
|---|---|---|---|---|
| 4 | Asn | 78 | 519[a] | 0.24, I (4:1) |
| 5 | Val | 48 | 504[a] | 0.36, I (9:1) |
| 6 | Phe[b] | 73 | 552 | 0.48, I (9:1) |
| 7 | Phe[c] | 89 | 552 | 0.30, I (9:1) |
| 8 | Ser—Phe—Asn | 78 | 753 | 0.14, I (4:1) |
| 8a | Phe—Val | 85 | 651 | 0.77, I (4:1) |

[a] = MS (DCI, NH$_3$) m/e = (M + H)$^+$
[b] = pure non-polar diastereomer
[c] = pure polar diastereomer

TABLE 2

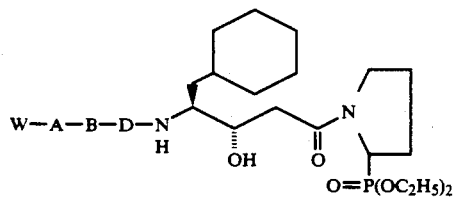

| Example No. | W—A—B—D | Yield (%) | MS (FAB) m/e (M + H)+ | R_f/eluent (ratio) | Starting material from Example |
|---|---|---|---|---|---|
| 9 | Boc—Val | 54 | 604 | 0.36, 0.42, I (93:7) | 2 |
| 10 | Boc—Phe | 62 | 658 | 0.15, 0.24, I (95:5) | 2 |
| 11 | CH$_3$(CH$_2$)$_{12}$CO—Phe—Asn | 29 | 876 | 0.21, I (9:1) | 4 |
| 12 | Boc—Phe—Asn | 30 | 766 | 0.30, I (9:1) | 4 |
| 13 | Boc—Ser—Phe—Asn | 18 | 853 | 0.27, I (9:1) | 4 |

EXAMPLE 14

Diethyl 1-{(3S,4S)-4-[(2S)-3-(tert-butylsulphonyl)2-(1-naphthylmethyl)propanoyl]-valinylamino-5-cyclohexyl-3-hydroxypentanoyl}-(2RorS)-2-(pyrrolidinyl)phosphonate

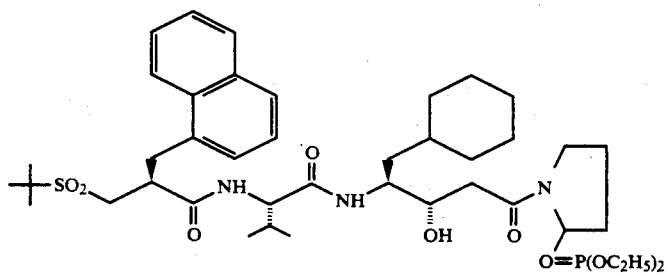

A stirred solution, cooled to 0° C., of 159 mg (0.48 mmol) of (2S)-3-tert-butylsulphonyl-2-(1-naphthylmethyl)propionic acid [prepared analogously to H. Bühlmayer et al., J. Med. Chem. 31, 1839 (1988)] and 71 mg (0.53 mmol) of HOBT in 5 ml of anhydrous dichloromethane was treated with 104 mg (0.50 mmol) of DCC and the mixture was stirred for 5 min. A solution of 250 mg (0.43 mmol) of the compound from Example 5 and 0.17 ml (1.5 mmol) of N-methylmorpholine in 5 ml of dichloromethane was then added dropwise. The cooling bath was removed and the reaction mixture was stirred at room temperature for 1 hour. The end of the reaction was determined by thin layer chromatography. The resulting urea was removed by filtration, the filtrate was concentrated in vacuo and the crude product was purified by chromatography on 41 g of silica gel (dichloromethane:methanol 95:5). 223 mg (63% of theory) of the title compound were obtained as a colourless foam.

R$_f$=0.39, I (95:5).
MS (FAB): m/e=820 (M+H)+, 842 (M+Na)+.
HPLC: pure diastereomer.

EXAMPLE 15

Diethyl 1-{(3S,4S)-4-[(2S)-2-benzyl-3-(tertbutylsulphonyl)-propanoyl]valinylamino]-5-cyclohexyl-3-hydroxypentanoyl}-(2R or S)-2-(pyrrolidinyl)phosphonate

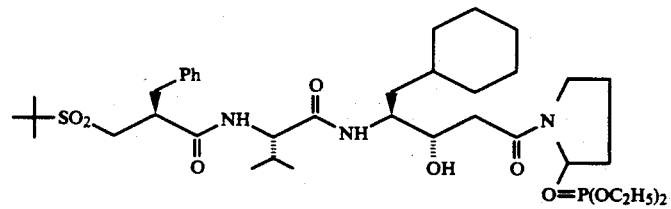

As described for Example 14, 146 mg (53% of theory) of the title compound were obtained as a colourless foam from 111 mg (0.39 mmol) of (S)-2-benzyl-3-(tert-butylsulphonyl)propionic acid [H. Bühlmayer et al., J. Med. Chem. 31, 1839 (1988)] and 205 mg (0.36 mmol) of the compound from Example 5, after chromatography of the crude product on 32 g of silica gel (I, 95:5).

R$_f$=0.41, I (95:5).
MS (FAB): m/e=770 (M+H)+, 792 (M+Na)+.

TABLE 3

[Structure: W—A—B—D—NH—CH(CH2-cyclohexyl)—CH(OH)—CH2—CO—N(pyrrolidine with 3-CH2—P(=O)(OC2H5)2)]

| Example No. | W—A—B—D— | 3-OH stereo-chemistry | Yield (%) | MS (FAB) m/e (M + H)+ | Rf/eluent (ratio) | Starting material from Example |
|---|---|---|---|---|---|---|
| 15a | Boc—Phe—Val | S | 56 | 751 | 0.30, I (93:7) | 2 |
| 15b | [1-naphthyl-CH2]2—CH—CO—Val | S | 63 | 827 | 0.24, I (95:5) | 5 |
| 15c | quinolin-2-yl—CO—Val | S | 86 | 659 | 0.08, I (95:5) | 5 |
| 15d | indol-2-yl—CO—Val | S | 60 | 647 | 0.05, I (95:5) | 5 |
| 15e | (CH3)3C—CH2CO—Phe—Val | S | 57 | 749 | 0.39, I (93:7) | 5 |
| 15f | CH3—C6H4—SO2—Phe—Val | S | 65 | 805 | 0.21, I (95:5) | 5 |
| 15g | Boc—Ser—Phe—Val | S | 70 | 838 | 0.05, I (93:7) | 5 |
| 15h | Boc—Phe—Gly—Gly | R | 57 | 766 | 0.12, I (9:1) | 29 |
| 15i | Boc—NH—C(CH3)2—CO—Val | S | 68 | 689 | 0.10, I (95:5) | 5 |
| 15j | Boc—NH—C(CH3)2—CO—Phe—Val | | | | | |
| 15k | [1-naphthyl-CH2]2—CH—CO—Val | R | 62 | 826 | 0.21, I (95:5) | 32 |
| 15l | quinolin-2-yl—CO—Val | R | 66 | 859 | 0.13, I (95:5) | 32 |
| 15m | indol-2-yl—CO—Val | R | 68 | 647 | 0.06, I (95:5) | 32 |

TABLE 3-continued

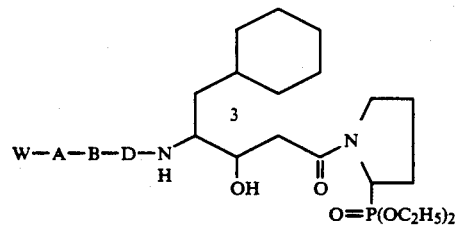

| Example No. | W—A—B—D— | 3-OH stereo- chemistry | Yield (%) | MS (FAB) m/e (M + H)+ | R$_f$/eluent (ratio) | Starting material from Example |
|---|---|---|---|---|---|---|
| 15n | ![naphthyl]CO—Val | R | 68 | 658 | 0.11, I (95:5) | 32 |

EXAMPLE 16

Diethyl 1-{(3S,4S)-5-cyclohexyl-3-hydroxy-4-(1-naphthylaminocarbonyl)phenylalaninyl]aminopentanoyl}-(2R or S)-2-(pyrrolidinyl)phosphonate

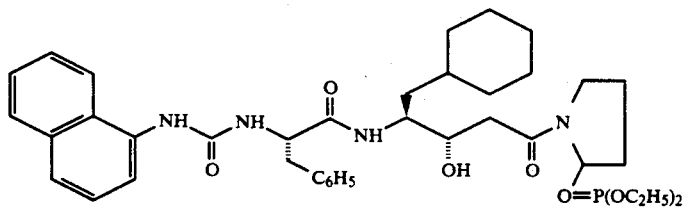

160 μl (1.14 mmol) of 1-naphthyl isocyanate were added dropwise to a stirred solution of 650 mg (1.03 mmol) of the compound from Example 7 and 290 μl (2.07 mmol) of triethylamine in 7 ml of anhydrous dichloromethane. After 15 min at room temperature, 5 ml of toluene were added and the reaction mixture was concentrated in vacuo. After chromatography of the residue on 40 g of silica gel (dichloromethane: methanol 95:5), 530 mg (71% of theory) of the title compound were obtained as a colourless rigid foam.

R$_f$=0.10, I (95:5).

MS (FAB): m/e=721 (M+H)+, 743 (M+Na)+.
HPLC: pure polar diastereomer.

As described for Example 16, the following products (Table 4) were obtained by reaction of various isocyanates with the appropriate amines:

TABLE 4

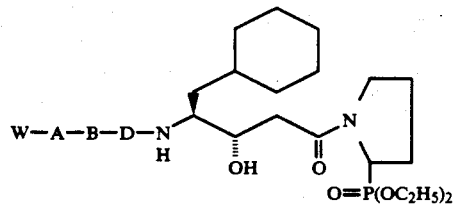

| Example No. | W—A—B—D | Yield (%) | MS (FAB) m/e (M + H)+ | R$_f$/eluent (ratio) | Starting material Example |
|---|---|---|---|---|---|
| 17 | 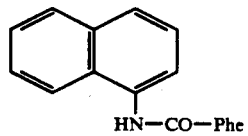 HN—CO—Phe | 57 | 721 | 0.19, I (95:5) | 6$^a$ |
| 18 | 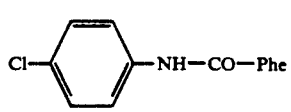 Cl—⟨⟩—NH—CO—Phe | 67 | 706 | 0.05, I (95:5) | 7 |

TABLE 4-continued

[Structure: W—A—B—D—NH—CH(CH2-cyclohexyl)—CH(OH)—CH2—C(O)—N(pyrrolidinyl with O=P(OC2H5)2)]

| Example No. | W—A—B—D | Yield (%) | MS (FAB) m/e (M + H)+ | Rf/eluent (ratio) | Starting material Example |
|---|---|---|---|---|---|
| 19 | cyclohexyl-NH—CO—Phe— | 59 | 678 | 0.27, I (93:7) | 7 |
| 20 | $CH_3(CH_2)_{11}NHCO$—Phe | 83 | 765 | 0.05, I (95:5) | 7 |
| 21 | $(CH_3)_3C$—NH—CO—Phe | 65 | 651 | 0.08, I (95:5) | 7 |
| 22 | cyclohexyl-NH—CO—Phe—Val | 34 | 776 | 0.18, 0.20, I (95:5) | 8a |
| 23 | naphthyl-NH—CO—Phe—Val | 37 | 821 | 0.20, 0.25, I (95:5) | 8a |

*non-polar diastereomer*

EXAMPLE 24

Diethyl 1-{(3S,4S)-4-[[(2-naphthoyl)phenylalaninyl]-valinylamino]-5-cyclohexyl-3-hydroxypentanonyl}-(2R,S)-2-(pyrrolidinyl)phosphonate

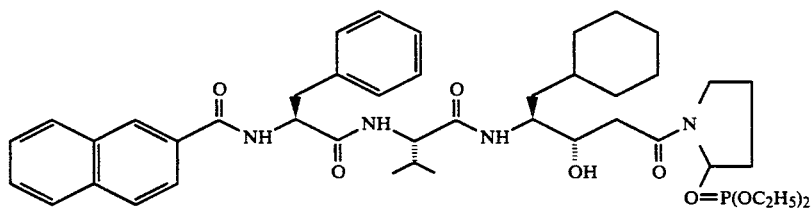

46 mg (0.24 mmol) of 2-naphthoyl chloride were added dropwise to a stirred solution, cooled to 0° C., of 148 mg (0.20 mmol) of the compound from Example 8a and 77 µl (0.7 mmol) of N-methylmorpholine in 1 ml of anhydrous dichloromethane. After 15 min, the mixture was poured into a mixture of 20 ml of cold sodium bicarbonate solution and 10 ml of ethyl acetate and thoroughly stirred. The organic phase was separated off, the aqueous phase was extracted with 10 ml of ethyl acetate and the combined organic extracts were dried over magnesium sulphate. After evaporation of the solvent in vacuo and chromatography of the crude product on 20 g of silica gel (dichloromethane:methanol 95:5), 91 mg (56% of theory) of the title compound were obtained as a colourless foam (mixture of the polar and non-polar diastereomer).

$R_f$=0.13, I (95:5).

MS (FAB): m/e=806 (M+H)+, 828 (M+Na)+.

TABLE 5

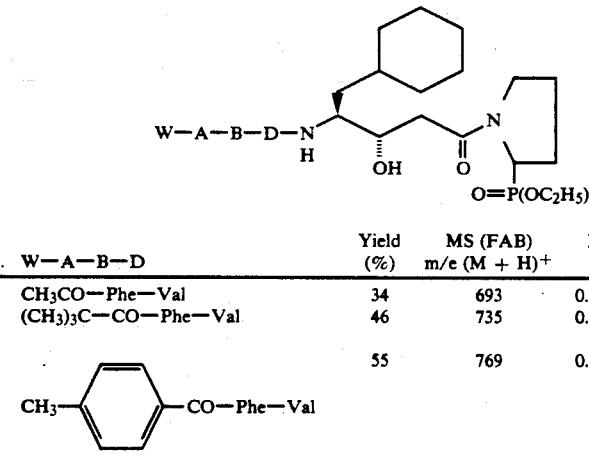

| Example No. | W—A—B—D | Yield (%) | MS (FAB) m/e (M + H)+ | R_f/eluent (ratio) | Starting material from Example |
|---|---|---|---|---|---|
| 25 | CH₃CO—Phe—Val | 34 | 693 | 0.13, I (93:7) | 8a |
| 26 | (CH₃)₃C—CO—Phe—Val | 46 | 735 | 0.05, I (95:5) | 8a |
| 27 | CH₃—⟨C₆H₄⟩—CO—Phe—Val | 55 | 769 | 0.13, I (95:5) | 8a |

EXAMPLE 28

Diethyl 1-{(3R,4S)-4-[(tert-butoxycarbonyl)amino]-5-cyclohexyl-3-hydroxypentanonyl]-(2R,S)-2-(pyrrolidinyl)phosphonate

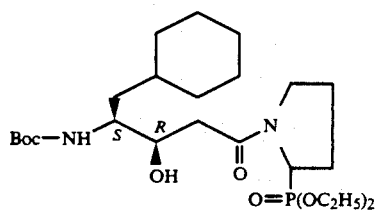

As described for Example 1, 3.24 g (65% of theory) of the title compound were obtained as a colourless foam from 3.12 g (9.89 mmol) of N-(tert-butoxycarbonyl)-(3R,4S)-4-amino-5-cyclohexyl-3-hydroxy-pentanoic acid [Boger et al., J. Med. Chem. 28, 1779 (1985)]and 2.25 g (10.88 mmol) of diethyl 2(R,S)-2-(pyrrolidinyl)-phosphonate [U.S. Pat. No. 4,186,268] after chromatography of the crude product on 160 g of silica gel (dichloromethane:methanol 95:5).

R_f=0.18, I (95:5).
MS (FAB): m/e=505 (M+H)+, 527 (M+Na)+.

EXAMPLE 29

Diethyl 1-[(3R,4S)-4-amino-5-cyclohexyl-3-hydroxypentanoyl]-(2R,S)-2-(pyrrolidinyl)phosphonate hydrochloride

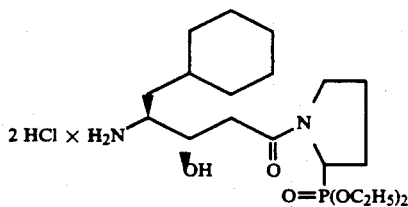

As described for Example 2, 2.04 g (83% of theory) of the title compound were obtained as a foam from 3.14 g (6.20 mmol) of the compound from Example 29.
R_f=0.18, IV.
MS (FAB): m/e=405 (M+H)+.

EXAMPLE 30

Diethyl 1-[(3R,4S)-4-(tert-butoxycarbonylvalinyl)amino-5-cyclohexyl-3-hydroxypentanonyl]-(2R,S)-2-(pyrrolidinyl)phosphonate

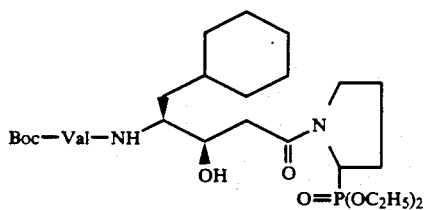

As described for Example 3, 1.387 q (65% of theory) of the title compound were obtained as a colourless foam from 1.70 g (3.56 mmol) of the compound from Example 29 and 0.85 g (3.92 mmol) of tert-butoxycarbonylvaline after chromatography of the crude product on 250 g of silica gel (dichloromethane : methanol 95:5).
R_f=0.06, I (95:5).
MS (FAB): m/e=604 (M+H)+, 626 (M+Na)+.

EXAMPLE 31

Diethyl 1-[(3R,4S)-5-cyclohexyl-3-hydroxy-4-valinylaminopentanoyl]-(2R,S)-2-(pyrrolidinyl)phosphonate hydrochloride

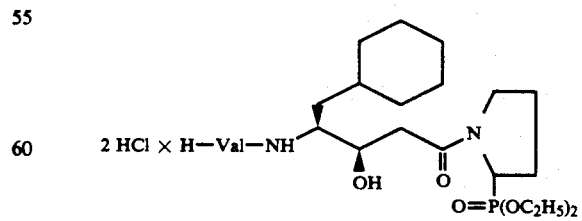

As described for Example 2, 1.225 g (97% of theory) of the title compound were obtained as a powder from 1.304 g (2.16 mmol) of the compound from Example 31.
R_f=0.39, IV
MS (FAB): m/e=504 (M+H)+.

(iii)
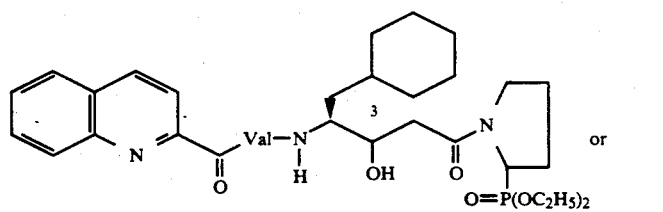
or
(iv)
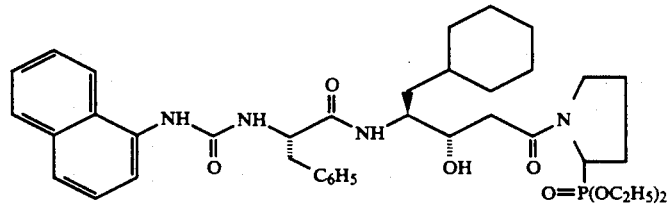

We claim:
1. Phosphonopyrrolidine- and piperidine-containing pseudopeptides of the general formula (I)

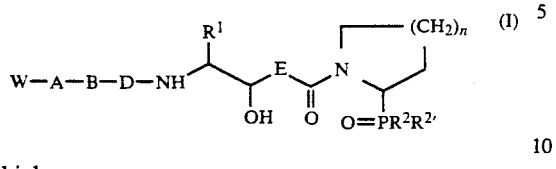

in which
W
  represents hydrogen or a typical amino protecting group, or
  represents straight-chain or branched alkyl or alkenyl in each case having up to 6 carbon atoms, which are optionally substituted by aryl having 6 to 10 carbon atoms, or
  represents a group of the formula $R^3$—CO—, $R^5R^4$N-CO— oe $R^6$—$SO_2$—, in which
  $R^3$
    denotes hydrogen, trifluoromethyl or straight-chain or branched alkoxy having up to 8 carbon atoms or alkyl having up to 18 carbon atoms, each of which is optionally monosubstituted or disubstituted by aryl having 6 to 10 carbon atoms or pyridyl, or
    denotes aryl having 6 to 10 carbon atoms, which is optionally substituted by halogen, trifluoromethyl, trifluoromethoxy or by straight-chain or branched alkyl having up to 8 carbon atoms,
    denotes cycloalkyl having 3 to 7 carbon atoms, or
    denotes quinolyl, indolyl, pyridyl, morpholino or piperazinyl, or
    denotes a radical of the formula

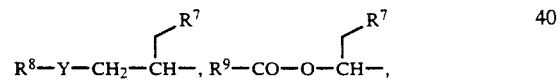

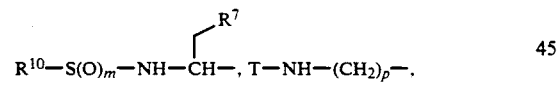

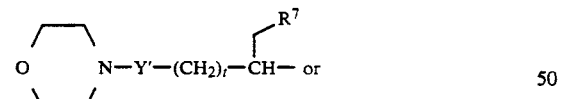

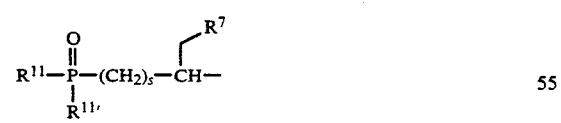

in which
  $R^7$ denotes phenyl or naphthyl,
  $R^8$, $R^9$ and $R^{10}$ are identical or different and denote straight-chain or branched alkyl having up to 17 carbon atoms, which is optionally substituted by phenyl or naphthyl, or denote aryl having 6 to 10 carbon atoms, which is in turn substituted by alkyl having up to 4 carbon atoms,
  m denotes a number 0, 1 or 2,
  T denotes morpholino or cyclohexyl,
  p denotes a number 1, 2 or 3,
  Y and Y' are identical or different and denote the CO or $SO_2$ group,
  t denotes a number 0 or 1,
  $R^{11}$ and $R^{11'}$ are identical or different and denote hydroxyl or alkoxy having up to 8 carbon atoms,
  s denotes a number 1 or 2,
$R^4$ and $R^5$ are identical or different and
  denote hydrogen or
  denote aryl having 6 to 10 carbon atoms, which is optionally substituted by straight-chain or branched alkyl having up to 6 carbon atoms or halogen, or
  denote cycloalkyl having 3 to 7 carbon atoms, or
  denote straight-chain or branched alkyl having up to 18 carbon atoms,
$R^6$ denotes straight-chain or branched alkyl having up to 4 carbon atoms or phenyl which can in turn be substituted by methyl,
A, B D are identical or different and
  represent a direct bond or
  represent a radical of the formula

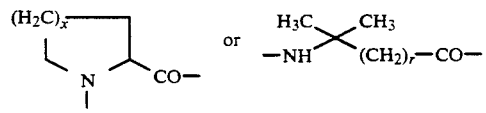

in which
  x denotes the number 1 or 2 and
  r denotes the number 0 or 1, or
  represent a group of the formula

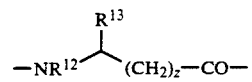

in which
  z denotes the number 0 or 1,
  $R^{12}$ denotes hydrogen or straight-chain or branched alkyl having up to 4 carbon atoms,
  $R^{13}$ denotes hydrogen, cycloalkyl having 3 to 8 carbon atoms or aryl having 6 to 10 carbon atoms, or denotes straight-chain or branched alkyl having up to 8 carbon atoms, which is optionally substituted by methylthio, hydroxyl, mercapto, guanidyl or by a group of the formula —$NR^{14}R^{15}$ or $R^{16}$—OC—, in which
    $R^{14}$ and $R^{15}$ are identical or different and denote hydrogen, straight-chain or branched alkyl having up to 8 carbon atoms or phenyl, and
    $R^{16}$ denotes hydroxyl, benzyloxy, alkoxy having up to 6 carbon atoms or the above-mentioned group —$NR^{14}R^{15}$,
  or which is optionally substituted by cycloalkyl having 3 to 8 carbon atoms or by aryl having 6 to 10 carbon atoms, which in turn is substituted by hydroxyl, halogen, nitro, alkoxy having up to 8 carbon atoms or by the group —$NR^{14}R^{15}$, in which
    $R^{14}$ and $R^{15}$ have the abovementioned meaning, or which is optionally substituted by a 5- or 6-membered nitrogen-containing heterocycle or indolyl, in which the corresponding —NH functions are optionally protected by alkyl having up to 6 carbon atoms or by an amino protecting group, $R^1$ represents straight-chain or branched alkyl or alkenyl having up to 10 carbon atoms, which are optionally substituted by cycloalkyl having 3 to 8 carbon atoms or by aryl having 6 to 10 carbon atoms, which can in turn be substituted by halogen, nitro, hydroxyl, amino or straight-chain or branched alkoxy having up to 4 carbon atoms, n represents the number 1 or 2, $R^2$ and $R^{2'}$ are identical or different and represent hydroxyl or alkoxy having up to 8 carbon atoms, and E represents a radical of the formula $CH_2$, $CF_2$, or $CH-OR^{17}$, in which
$R^{17}$ denotes hydrogen or straight-chain or branched alkyl having up to 4 carbon atoms, and their physiologically acceptable salts.

2. Compounds of the formula (I) in which according to claim 1,

W represents hydrogen, tert-butyloxycarbonyl (BOC), 9-fluorenylmethyloxycarbonyl (Fmoc) or benzyloxycarbonyl or represents straight-chain or branched alkyl or alkenyl in each case having up to 4 carbon atoms, which are optionally substituted by phenyl, or represents a group of the formula $R^3$—CO—, $R^5R^4N$—CO— or $R^6$—$SO_2$—, in which
$R^3$ denotes hydrogen, trifluoromethyl or straight-chain or branched alkoxy having up to 4 carbon atoms or alkyl having up to 16 carbon atoms, each of which is optionally monosubstituted or disubstituted by phenyl, naphthyl or pyridyl, or denotes phenyl or naphthyl, which are optionally substituted by fluorine, chlorine, trifluoromethyl, trifluoromethoxy or by straight-chain or branched alkyl having up to 6 carbon atoms, denotes cyclopropyl, cyclopentyl, cyclohexyl, quinolyl, indolyl, pyridyl, morpholino or piperazinyl, or denotes a radical of the formula

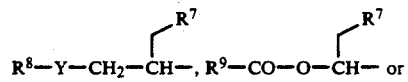

in which
Y denotes the CO or $SO_2$ group,
$R^7$ denotes phenyl or naphthyl,
$R^8$, $R^9$ and $R^{10}$ are identical or different and denote straight-chain or branched alkyl having up to 15 carbon atoms, tolyl, phenyl or naphthyl,
m denotes a number 1 or 2,
$R^4$ and $R^5$ are identical or different and denote hydrogen or
denote phenyl or naphthyl, which are optionally substituted by straight-chain or branched alkyl having up to 4 carbon atoms, fluorine or chlorine, denote cyclopropyl, cyclopentyl or cyclohexyl, or denote straight-chain or branched alkyl having up to 16 carbon atoms, $R^6$ denotes phenyl which is substituted by methyl, A, B and D are identical or different and
represent a direct bond or
represent proline, or
represent a radical of the formula

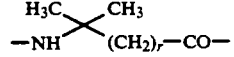

in which
r denotes the number 0 or 1,
represent a group of the formula

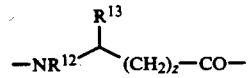

in which
z denotes the number 0 or 1,
$R^{12}$ denotes hydrogen, methyl or ethyl,
$R^{13}$ denotes hydrogen, cyclopentyl, cyclohexyl or phenyl,
or denotes straight-chain or branched alkyl having up to 6 carbon atoms, which can optionally be substituted by methylthio, hydroxyl, mercapto, guanidyl, amino, carboxyl or $H_2N$—CO—, or is substituted by cyclohexyl, naphthyl or phenyl, each of which can in turn be substituted by fluorine, hydroxyl, nitro or alkoxy having up to 4 carbon atoms, or is substituted by indolyl, imidazolyl, pyridyl, triazolyl or pyrazolyl, where the corresponding —NH functions are optionally protected by alkyl having up to 4 carbon atoms or by an amino protecting group, $R^1$ represents straight-chain or branched alkyl or alkenyl having up to 8 carbon atoms, which are optionally substituted by cyclopropyl, cyclobutyl, cyclopentyl, cyclohexyl, cycloheptyl or phenyl, each of which is in turn substituted by fluorine, chlorine, bromine, nitro, hydroxyl or amino, n represents the number 1 or 2, $R^2$ and $R^{2'}$ are identical or different and
represent hydroxyl or alkoxy having up to 6 carbon atoms, and E represents a radical of the formula $>CH_2$, $>CF_2$ or $>CH-OR^{17}$, in which
$R^{17}$ denotes hydrogen or straight-chain or branched alkyl having up to 4 carbon atoms, and their physiologically acceptable salts.

3. Compounds of the formula (I) according to claim 1, in which

W
represents hydrogen, tert-butyloxycarbonyl (BOC) or benzyloxycarbonyl, or
represents allyl or benzyl,
represents a group of the formula $R^3$—CO—, $R^5R^4N$—CO— or $R^6$—$SO_2$—, in which
$R^3$ denotes hydrogen, trifluoromethyl or straight-chain or branched alkyl having up to 14 carbon atoms, each of which is optionally monosubstituted or disubstituted by phenyl, naphthyl or pyridyl, or denotes phenyl or naphthyl, which are optionally substituted by fluorine, chlorine, trifluoromethyl, trifluoromethoxy or by straight-chain or branched alkyl having up to 4 carbon atoms, denotes cyclopropyl, cyclopentyl, cyclohexyl, quinolyl, indolyl, pyridyl, morpholino or piperazinyl, or denotes a radical of the formula

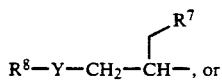

or

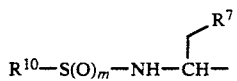

in which
Y denotes the CO or $SO_2$ group,
$R^7$ denotes phenyl or naphthyl,
$R^8$ and $R^{10}$ are identical or different and denote straight-chain or branched alkyl having up to 14 carbon atoms, tolyl, phenyl or naphthyl, m - denotes a number 1 or 2, $R^4$ and $R^5$ are identical or different and
denote hydrogen or
denote phenyl or naphthyl, which are optionally substituted by methyl, fluorine or chlorine,
denote cyclopropyl, cyclopentyl or cyclohexyl, or
denote straight-chain or branched alkyl having up to 14 carbon atoms, $R^6$ denotes phenyl which is substituted by methyl,
A, B and D are identical or different and
represent a direct bond, or
represent proline, or
represent a radical of the formula

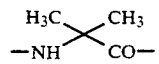

represent a group of the formula

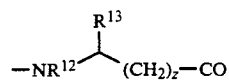

in which
z denotes the number 0 or 1,
$R^{12}$ denotes hydrogen or methyl,
$R^{13}$ denotes hydrogen, cyclopentyl or cyclohexyl,
or denotes straight-chain or branched alkyl having up to 4 carbon atoms, which is optionally substituted by methylthio, hydroxyl, mercapto, guanidyl, amino, carboxyl or $H_2N-CO-$, or is substituted by cyclohexyl, naphthyl or phenyl, each of which can in turn be substituted by hydroxyl, fluorine, chlorine or alkoxy having up to 4 carbon atoms, or is substituted by indolyl, imidazolyl, triazolyl, pyridyl or pyrazolyl, where the NH function is optionally protected by methyl, benzyloxymethylene or $R^1$ represents straight-chain or branched alkyl having up to 6 carbon atoms, which is optionally substituted by cyclopropyl, cyclopentyl, cyclohexyl or phenyl, each of which can in turn be substituted by hydroxyl, n represents the number 1 or 2,
$R^2$ and $R^{2'}$ are identical or different and
represent hydroxyl or alkoxy having up to 4 carbon atoms,
and
represents the $>CH_2$ or the $>CHOH$ group and their physiologically acceptable salts.

4. A compound according to claim 1 having the formula

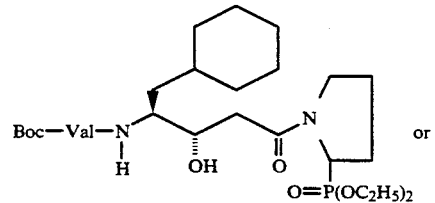

(i)

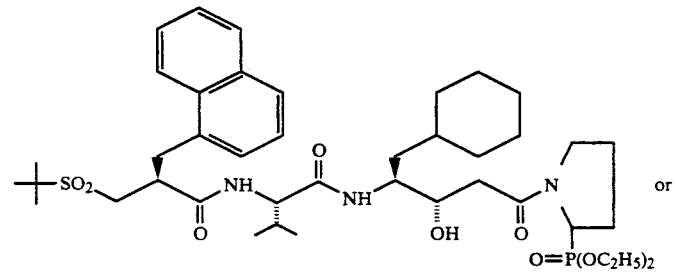

(ii)